United States Patent
Lim et al.

(10) Patent No.: US 7,375,210 B2
(45) Date of Patent: May 20, 2008

(54) PCR PRIMER SET FOR DETECTING SEVERE ACUTE RESPIRATORY SYNDROME (SARS)-CORONAVIRUS, METHOD AND KIT FOR DETECTING SARS-CORONAVIRUS USING THE SAME

(75) Inventors: Hee-kyun Lim, Suwon-si (KR); Sang-hyo Kim, Yongin-si (KR); Jung-joo Hwang, Suwon-si (KR); Young-sun Lee, Seongnam-si (KR); Young-a Kim, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 371 days.

(21) Appl. No.: 10/997,462

(22) Filed: Nov. 24, 2004

(65) Prior Publication Data
US 2008/0096186 A1    Apr. 24, 2008

(30) Foreign Application Priority Data
Dec. 12, 2003 (KR) .................. 10-2003-0090559

(51) Int. Cl.
*C07H 21/04* (2006.01)
(52) U.S. Cl. .................. 536/24.33; 435/6; 435/91.2
(58) Field of Classification Search .................. None
See application file for complete search history.

(56) References Cited

U.S. PATENT DOCUMENTS

2006/0240530 A1* 10/2006 Baric et al. .................. 435/91.1
2006/0257852 A1* 11/2006 Rappuoli et al. .............. 435/5

OTHER PUBLICATIONS

Li et al., "Severe Acute Respiratory syndrome-associated coronavirus genotype and its characterization", Chinese Medical Journal, 2003, 116(9), p. 1288-1292.*

* cited by examiner

*Primary Examiner*—Gary Benzion
*Assistant Examiner*—Stephanie K. Mummert
(74) *Attorney, Agent, or Firm*—Cantor Colburn LLP

(57) ABSTRACT

Provided are SARS-CoV detection PCR primers having nucleotide sequences as set forth in SEQ ID NOS: 1-46, a method for detecting SARS-CoV using the primers, and a SARS-CoV detection kit including the primers.

9 Claims, 2 Drawing Sheets

SEQUENCE LISTING

<160> NUMBER OF SEQ ID NOS: 42

<210> SEQ ID NO 1
<211> LENGTH: 26
<212> TYPE: DNA
<213> ORGANISM: Artificial Sequence
<220> FEATURE:
<223> OTHER INFORMATION: primer

<400> SEQUENCE: 1
gaggaagact ggctggatga tactac                    26

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
actttgtgcc tccttaacga tgtc                      24

<210> SEQ ID NO 3
<211> LENGTH: 25
<212> TYPE: DNA
<213> ORGANISM: Artificial Sequence
<220> FEATURE:
<223> OTHER INFORMATION: primer

<400> SEQUENCE: 3
ttatgattgc gtgtctttct gctat                     25

<210> SEQ ID NO 4
<211> LENGTH: 25
<212> TYPE: DNA

```
<213> ORGANISM: Artificial Sequence
<220> FEATURE:
<223> OTHER INFORMATION: primer

<400> SEQUENCE: 4
tgccacaagg ttaaagtcat tcaaa                                              25

<210> SEQ ID NO 5
<211> LENGTH: 22
<212> TYPE: DNA
<213> ORGANISM: Artificial Sequence
<220> FEATURE:
<223> OTHER INFORMATION: primer

<400> SEQUENCE: 5
tcaagcgtgg caaccaggtg tt                                                 22

<210> SEQ ID NO 6
<211> LENGTH: 24
<212> TYPE: DNA
<213> ORGANISM: Artificial Sequence
<220> FEATURE:
<223> OTHER INFORMATION: primer

<400> SEQUENCE: 6
ttggcaacca ttgtctgagc acag                                               24

<210> SEQ ID NO 7
<211> LENGTH: 25
<212> TYPE: DNA
<213> ORGANISM: Artificial Sequence
<220> FEATURE:
<223> OTHER INFORMATION: primer

<400> SEQUENCE: 7
catttggtgc tggcgctgct cttca                                              25

<210> SEQ ID NO 8
<211> LENGTH: 27
<212> TYPE: DNA
<213> ORGANISM: Artificial Sequence
<220> FEATURE:
<223> OTHER INFORMATION: primer

<400> SEQUENCE: 8
ggttggcgat ttgttttttgg ttctcat                                           27

<210> SEQ ID NO 9
<211> LENGTH: 26
<212> TYPE: DNA
<213> ORGANISM: Artificial Sequence
<220> FEATURE:
<223> OTHER INFORMATION: primer

<400> SEQUENCE: 9
agcttaaaca actcctggaa caatgg                                             26

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
gtagacagca gcaagcacaa aaca                                               24
```

-continued

```
<210> SEQ ID NO 11
<211> LENGTH: 26
<212> TYPE: DNA
<213> ORGANISM: Artificial Sequence
<220> FEATURE:
<223> OTHER INFORMATION: primer

<400> SEQUENCE: 11
tggcacccgc aatcctaata acaatg                                        26

<210> SEQ ID NO 12
<211> LENGTH: 23
<212> TYPE: DNA
<213> ORGANISM: Artificial Sequence
<220> FEATURE:
<223> OTHER INFORMATION: primer

<400> SEQUENCE: 12
actgccgcct ctgcttccct ctg                                           23

<210> SEQ ID NO 13
<211> LENGTH: 24
<212> TYPE: DNA
<213> ORGANISM: Artificial Sequence
<220> FEATURE:
<223> OTHER INFORMATION: primer

<400> SEQUENCE: 13
ttgagccaga accagaacct acac                                          24

<210> SEQ ID NO 14
<211> LENGTH: 22
<212> TYPE: DNA
<213> ORGANISM: Artificial Sequence
<220> FEATURE:
<223> OTHER INFORMATION: primer

<400> SEQUENCE: 14
gcacctgcta caccaccacc at                                            22

<210> SEQ ID NO 15
<211> LENGTH: 25
<212> TYPE: DNA
<213> ORGANISM: Artificial Sequence
<220> FEATURE:
<223> OTHER INFORMATION: primer

<400> SEQUENCE: 15
ttatgattgc gtgtctttct gctat                                         25

<210> SEQ ID NO 16
<211> LENGTH: 26
<212> TYPE: DNA
<213> ORGANISM: Artificial Sequence
<220> FEATURE:
<223> OTHER INFORMATION: primer

<400> SEQUENCE: 16
ccacaaggtt aaagtcattc aaagta                                        26

<210> SEQ ID NO 17
<211> LENGTH: 26
<212> TYPE: DNA
<213> ORGANISM: Artificial Sequence
<220> FEATURE:
```

```
<223> OTHER INFORMATION: primer

<400> SEQUENCE: 17
caagtcaagc gtggcaacca ggtgtt                                          26

<210> SEQ ID NO 18
<211> LENGTH: 26
<212> TYPE: DNA
<213> ORGANISM: Artificial Sequence
<220> FEATURE:
<223> OTHER INFORMATION: primer

<400> SEQUENCE: 18
gccagttggc aaccattgtc tgagca                                          26

<210> SEQ ID NO 19
<211> LENGTH: 23
<212> TYPE: DNA
<213> ORGANISM: Artificial Sequence
<220> FEATURE:
<223> OTHER INFORMATION: primer

<400> SEQUENCE: 19
ccaaaaacaa atcgccaacc aat                                             23

<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20
gtacctccgc ctcgacttta tcaa                                            24

<210> SEQ ID NO 21
<211> LENGTH: 25
<212> TYPE: DNA
<213> ORGANISM: Artificial Sequence
<220> FEATURE:
<223> OTHER INFORMATION: primer

<400> SEQUENCE: 21
gattgctgcc tacactgctg ctcta                                           25

<210> SEQ ID NO 22
<211> LENGTH: 24
<212> TYPE: DNA
<213> ORGANISM: Artificial Sequence
<220> FEATURE:
<223> OTHER INFORMATION: primer

<400> SEQUENCE: 22
tggcgatttg tttttggttc tcat                                            24

<210> SEQ ID NO 23
<211> LENGTH: 26
<212> TYPE: DNA
<213> ORGANISM: Artificial Sequence
<220> FEATURE:
<223> OTHER INFORMATION: primer

<400> SEQUENCE: 23
agcttaaaca actcctggaa caatgg                                          26
```

```
<210> SEQ ID NO 24
<211> LENGTH: 27
<212> TYPE: DNA
<213> ORGANISM: Artificial Sequence
<220> FEATURE:
<223> OTHER INFORMATION: primer

<400> SEQUENCE: 24
aaacagcctg aaggaagcaa cgaagta                                          27

<210> SEQ ID NO 25
<211> LENGTH: 24
<212> TYPE: DNA
<213> ORGANISM: Artificial Sequence
<220> FEATURE:
<223> OTHER INFORMATION: primer

<400> SEQUENCE: 25
agggaagcag aggcggcagt caag                                             24

<210> SEQ ID NO 26
<211> LENGTH: 24
<212> TYPE: DNA
<213> ORGANISM: Artificial Sequence
<220> FEATURE:
<223> OTHER INFORMATION: primer

<400> SEQUENCE: 26
aatagcgcga gggcagtttc acca                                             24

<210> SEQ ID NO 27
<211> LENGTH: 22
<212> TYPE: DNA
<213> ORGANISM: Artificial Sequence
<220> FEATURE:
<223> OTHER INFORMATION: primer

<400> SEQUENCE: 27
ggaagcagag gcggcagtca ag                                               22

<210> SEQ ID NO 28
<211> LENGTH: 21
<212> TYPE: DNA
<213> ORGANISM: Artificial Sequence
<220> FEATURE:
<223> OTHER INFORMATION: primer

<400> SEQUENCE: 28
agcgcgaggg cagtttcacc a                                                21

<210> SEQ ID NO 29
<211> LENGTH: 24
<212> TYPE: DNA
<213> ORGANISM: Artificial Sequence
<220> FEATURE:
<223> OTHER INFORMATION: primer

<400> SEQUENCE: 29
atgaattacc aagtcaatgg ttac                                             24

<210> SEQ ID NO 30
<211> LENGTH: 21
<212> TYPE: DNA
<213> ORGANISM: Artificial Sequence
<220> FEATURE:
<223> OTHER INFORMATION: primer
```

<400> SEQUENCE: 30
cataaccagt cggtacagct a                           21

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
gaagctattc gtcacgttcg                             20

<210> SEQ ID NO 32
<211> LENGTH: 22
<212> TYPE: DNA
<213> ORGANISM: Artificial Sequence
<220> FEATURE:
<223> OTHER INFORMATION: primer

<400> SEQUENCE: 32
ctgtagaaaa tcctagctgg ag                          22

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
cctctcttgt tcttgctcgc a                           21

<210> SEQ ID NO 34
<211> LENGTH: 21
<212> TYPE: DNA
<213> ORGANISM: Artificial Sequence
<220> FEATURE:
<223> OTHER INFORMATION: primer

<400> SEQUENCE: 34
tatagtgagc cgccacacat g                           21

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
ctaacatgct taggataatg c                           21

<210> SEQ ID NO 36
<211> LENGTH: 21
<212> TYPE: DNA
<213> ORGANISM: Artificial Sequence
<220> FEATURE:
<223> OTHER INFORMATION: primer

<400> SEQUENCE: 36
caggtaagcg taaaactcat c                           21

<210> SEQ ID NO 37
<211> LENGTH: 21

```
<212> TYPE: DNA
<213> ORGANISM: Artificial Sequence
<220> FEATURE:
<223> OTHER INFORMATION: primer

<400> SEQUENCE: 37
gcctctcttg ttcttgctcg c                                              21

<210> SEQ ID NO 38
<211> LENGTH: 21
<212> TYPE: DNA
<213> ORGANISM: Artificial Sequence
<220> FEATURE:
<223> OTHER INFORMATION: primer

<400> SEQUENCE: 38
caggtaagcg taaaactcat c                                              21

<210> SEQ ID NO 39
<211> LENGTH: 26
<212> TYPE: DNA
<213> ORGANISM: Artificial Sequence
<220> FEATURE:
<223> OTHER INFORMATION: primer

<400> SEQUENCE: 39
caccgtttct acaggttagc taacga                                         26

<210> SEQ ID NO 40
<211> LENGTH: 26
<212> TYPE: DNA
<213> ORGANISM: Artificial Sequence
<220> FEATURE:
<223> OTHER INFORMATION: primer

<400> SEQUENCE: 40
aaatgtttac gcaggtaagc gtaaaa                                         26

<210> SEQ ID NO 41
<211> LENGTH: 17
<212> TYPE: DNA
<213> ORGANISM: Artificial Sequence
<220> FEATURE:
<223> OTHER INFORMATION: primer

<400> SEQUENCE: 41
tacacacctc agcgttg                                                   17

<210> SEQ ID NO 42
<211> LENGTH: 16
<212> TYPE: DNA
<213> ORGANISM: Artificial Sequence
<220> FEATURE:
<223> OTHER INFORMATION: primer

<400> SEQUENCE: 42
cacgaacgtg acgaat                                                    16
```

PCR PRIMER SET FOR DETECTING SEVERE ACUTE RESPIRATORY SYNDROME (SARS)-CORONAVIRUS, METHOD AND KIT FOR DETECTING SARS-CORONAVIRUS USING THE SAME

This application claims priority from Korean Patent Application No. 2003-90559, filed on Dec. 12, 2003, in the Korean Intellectual Property Office, the disclosure of which is incorporated herein in its entirety by reference.

BACKGROUND OF THE INVENTION

1. Field of the Invention

The present invention relates to PCR primer sets for detecting severe acute respiratory syndrome (SARS) virus, a method and a kit for detecting SARS virus.

2. Description of the Related Art

Severe acute respiratory syndrome (SARS) virus is a new type of coronavirus and is designated as SARS-Coronavirus (hereinafter, referred to as "SARS-CoV") by the World Health Organization (WHO). It is known that SARS-CoV gives rise to severe acute respiratory syndrome. SARS-CoV is a novel RNA virus. It is known that the whole genome sequence of SARS-CoV consists of about 29,730 bp and the genetic makeup is similar to those of other types of coronaviruses.

The WHO reported guidelines for laboratory diagnosis of SARS as follows: (a) antibody test: identification of SARS-CoV antibody in serum after one day, (b) PCR (Polymerase Chain Reaction) test: identification of SARS-CoV RNA by PCR, and (c) virus separation: separation of SARS-CoV.

In a conventional PCR test, the following six types of primers are used for detection of SARS-CoV:

(1) BNIoutS2: SEQ ID NO: 29 (24mer); BNIoutAs: SEQ ID NO: 30 (21mer), BNIinS: SEQ ID NO: 31 (20mer); BNIinAs: SEQ ID NO: 32 (22mer),
(2) SAR1S: SEQ ID NO: 33 (21mer); SAR1As: SEQ ID NO: 34 (21mer),
(3) Cor-p-F2: SEQ ID NO: 35 (21 mer); Cor-p-R1: SEQ ID NO: 34 (21 mer),
(4) Cor-p-F3: SEQ ID NO: 35 (21mer); Cor-p-R1: SEQ ID NO: 36 (21mer),
(5) COR-1: SEQ ID NO: 37 (26mer); COR-2: SEQ ID NO: 38 (26mer),
(6) HKU (sense): SEQ ID NO: 39 (17mer); HKU (antisense): SEQ ID NO: 40 (16mer).

Among them, the primers of (1), which were developed by Bernhard-Nocht Institute (BNI, Germany) for diagnosis of SARS generated in early 2003, have been most widely used. However, only a local region, i.e., a polymerase gene region, of the whole genome sequence of about 30 kb of SARS-CoV, is used as a target site of currently known primers. Such a narrow application site may lead to either false negative or false positive results.

In view of these problems, the present inventors found SARS-CoV-specific primers which reduce a likelihood of being determined as false negative or false positive and rapidly detect SARS-CoV in situ after rapid PCR, and completed the present invention.

SUMMARY OF THE INVENTION

The present invention provides SARS-CoV-specific primer sets.

The present invention also provides a method for specifically detecting SARS-CoV using the primer sets.

The present invention also provides a SARS-CoV detection kit including the primer set.

According to an aspect of the present invention, there is provided a PCR primer set for SARS-CoV detection selected from the group consisting of the following primer sets: (a) a primer set (GS-SARS01) including a primer having a nucleotide sequence as set forth in SEQ ID NO: 1 and a primer having a nucleotide sequence as set forth in SEQ ID NO: 2; (b) a primer set (GS-SARS02) including a primer having a nucleotide sequence as set forth in SEQ ID NO: 3 and a primer having a nucleotide sequence as set forth in SEQ ID NO: 4; (c) a primer set (GS-SARS03) including a primer having a nucleotide sequence as set forth in SEQ ID NO: 5 and a primer having a nucleotide sequence as set forth in SEQ ID NO: 6; (d) a primer set (GS-SARS04) including a primer having a nucleotide sequence as set forth in SEQ ID NO: 7 and a primer having a nucleotide sequence as set forth in SEQ ID NO: 8; (e) a primer set (GS-SARS05) including a primer having a nucleotide sequence as set forth in SEQ ID NO: 9 and a primer having a nucleotide sequence as set forth in SEQ ID NO: 10; (f) a primer set (GS-SARS06) including a primer having a nucleotide sequence as set forth in SEQ ID NO: 11 and a primer having a nucleotide sequence as set forth in SEQ ID NO: 12; (g) a primer set (GS-SARS07) including a primer having a nucleotide sequence as set forth in SEQ ID NO: 13 and a primer having a nucleotide sequence as set forth in SEQ ID NO: 14; (h) a primer set (GS-SARS08) including a primer having a nucleotide sequence as set forth in SEQ ID NO: 15 and a primer having a nucleotide sequence as set forth in SEQ ID NO: 16; (i) a primer set (GS-SARS09) including a primer having a nucleotide sequence as set forth in SEQ ID NO: 17 and a primer having a nucleotide sequence as set forth in SEQ ID NO: 18; (j) a primer set (GS-SARS10) including a primer having a nucleotide sequence as set forth in SEQ ID NO: 19 and a primer having a nucleotide sequence as set forth in SEQ ID NO: 20; (k) a primer set (GS-SARS11) including a primer having a nucleotide sequence as set forth in SEQ ID NO: 21 and a primer having a nucleotide sequence as set forth in SEQ ID NO: 22; (l) a primer set (GS-SARS12) including a primer having a nucleotide sequence as set forth in SEQ ID NO: 23 and a primer having a nucleotide sequence as set forth in SEQ ID NO: 24; (m) a primer set (GS-SARS13) including a primer having a nucleotide sequence as set forth in SEQ ID NO: 25 and a primer having a nucleotide sequence as set forth in SEQ ID NO: 26; (n) a primer set (GS-SARS14) including a primer having a nucleotide sequence as set forth in SEQ ID NO: 27 and a primer having a nucleotide sequence as set forth in SEQ ID NO: 28; (o) a primer set (GS-SARS15) including a primer having a nucleotide sequence as set forth in SEQ ID NO: 29 and a primer having a nucleotide sequence as set forth in SEQ ID NO: 30; (p) a primer set (GS-SARS16) including a primer having a nucleotide sequence as set forth in SEQ ID NO: 31 and a primer having a nucleotide sequence as set forth in SEQ ID NO: 32; (q) a primer set (GS-SARS17) including a primer having a nucleotide sequence as set forth in SEQ ID NO: 33 and a primer having a nucleotide sequence as set forth in SEQ ID NO: 34; (r) a primer set (GS-SARS18) including a primer having a nucleotide sequence as set forth in SEQ ID NO: 35 and a primer having a nucleotide sequence as set forth in SEQ ID NO: 36; (s) a primer set (GS-SARS19) including a primer having a nucleotide sequence as set forth in SEQ ID NO: 37 and a primer having a nucleotide sequence as set forth in SEQ ID NO: 38; (t) a primer set (GS-SARS20) including a primer having a nucleotide sequence as set forth in SEQ ID NO: 39 and a primer having a nucleotide sequence as set forth in SEQ ID NO: 40; (u) a primer set (GS-SARS21) including a primer having a nucleotide sequence as set forth in SEQ ID NO: 41 and a primer having a nucleotide sequence as set forth in SEQ ID NO: 42; (v) a primer set (GS-SARS22) including a primer having a nucleotide sequence as set forth in SEQ ID NO: 43 and a primer having a nucleotide sequence as set forth in SEQ ID NO: 44; and (w) a primer set (GS-SARS23) including a primer having a nucleotide sequence as set forth in SEQ ID NO: 45 and a primer having a nucleotide sequence as set forth in SEQ ID NO: 46.

According to another aspect of the present invention, there is provided a method for detecting SARS-CoV, which includes amplifying a nucleic acid sample obtained from an individual by PCR using the primer set.

According to yet another aspect of the present invention, there is provided a SARS-CoV detection kit including the primer set.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
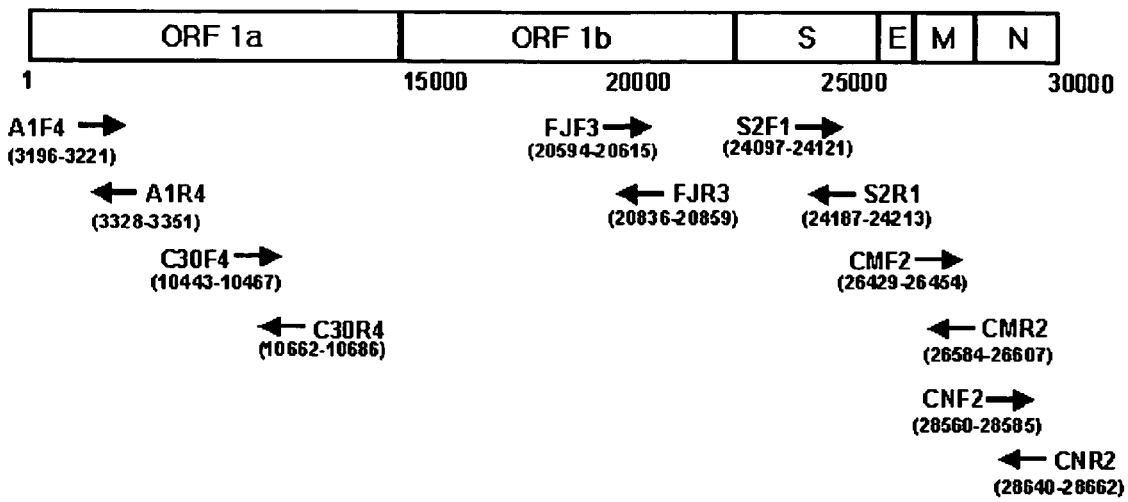
FIG. 1 schematically illustrates target nucleotide sequences for PCR primers according to the present invention.

The present invention provides a PCR primer set selected from the group consisting of the following primer sets:

(a) a primer set (GS-SARS01) including a primer having a nucleotide sequence as set forth in SEQ ID NO: 1 and a primer having a nucleotide sequence as set forth in SEQ ID NO: 2;

(b) a primer set (GS-SARS02) including a primer having a nucleotide sequence as set forth in SEQ ID NO: 3 and a primer having a nucleotide sequence as set forth in SEQ ID NO: 4;

(c) a primer set (GS-SARS03) including a primer having a nucleotide sequence as set forth in SEQ ID NO: 5 and a primer having a nucleotide sequence as set forth in SEQ ID NO: 6;

(d) a primer set (GS-SARS04) including a primer having a nucleotide sequence as set forth in SEQ ID NO: 7 and a primer having a nucleotide sequence as set forth in SEQ ID NO: 8;

(e) a primer set (GS-SARS05) including a primer having a nucleotide sequence as set forth in SEQ ID NO: 9 and a primer having a nucleotide sequence as set forth in SEQ ID NO: 10;

(f) a primer set (GS-SARS06) including a primer having a nucleotide sequence as set forth in SEQ ID NO: 11 and a primer having a nucleotide sequence as set forth in SEQ ID NO: 12;

(g) a primer set (GS-SARS07) including a primer having a nucleotide sequence as set forth in SEQ ID NO: 13 and a primer having a nucleotide sequence as set forth in SEQ ID NO: 14;

(h) a primer set (GS-SARS08) including a primer having a nucleotide sequence as set forth in SEQ ID NO: 15 and a primer having a nucleotide sequence as set forth in SEQ ID NO: 16;

(i) a primer set (GS-SARS09) including a primer having a nucleotide sequence as set forth in SEQ ID NO: 17 and a primer having a nucleotide sequence as set forth in SEQ ID NO: 18;

(j) a primer set (GS-SARS10) including a primer having a nucleotide sequence as set forth in SEQ ID NO: 19 and a primer having a nucleotide sequence as set forth in SEQ ID NO: 20;

(k) a primer set (GS-SARS11) including a primer having a nucleotide sequence as set forth in SEQ ID NO: 21 and a primer having a nucleotide sequence as set forth in SEQ ID NO: 22;

(l) a primer set (GS-SARS12) including a primer having a nucleotide sequence as set forth in SEQ ID NO: 23 and a primer having a nucleotide sequence as set forth in SEQ ID NO: 24;

(m) a primer set (GS-SARS13) including a primer having a nucleotide sequence as set forth in SEQ ID NO: 25 and a primer having a nucleotide sequence as set forth in SEQ ID NO: 26;

(n) a primer set (GS-SARS14) including a primer having a nucleotide sequence as set forth in SEQ ID NO: 27 and a primer having a nucleotide sequence as set forth in SEQ ID NO: 28;

(o) a primer set (GS-SARS15) including a primer having a nucleotide sequence as set forth in SEQ ID NO: 29 and a primer having a nucleotide sequence as set forth in SEQ ID NO: 30;

(p) a primer set (GS-SARS16) including a primer having a nucleotide sequence as set forth in SEQ ID NO: 31 and a primer having a nucleotide sequence as set forth in SEQ ID NO: 32;

(q) a primer set (GS-SARS17) including a primer having a nucleotide sequence as set forth in SEQ ID NO: 33 and a primer having a nucleotide sequence as set forth in SEQ ID NO: 34;

(r) a primer set (GS-SARS18) including a primer having a nucleotide sequence as set forth in SEQ ID NO: 35 and a primer having a nucleotide sequence as set forth in SEQ ID NO: 36;

(s) a primer set (GS-SARS19) including a primer having a nucleotide sequence as set forth in SEQ ID NO: 37 and a primer having a nucleotide sequence as set forth in SEQ ID NO: 38;

(t) a primer set (GS-SARS20) including a primer having a nucleotide sequence as set forth in SEQ ID NO: 39 and a primer having a nucleotide sequence as set forth in SEQ ID NO: 40;

(u) a primer set (GS-SARS21) including a primer having a nucleotide sequence as set forth in SEQ ID NO: 41 and a primer having a nucleotide sequence as set forth in SEQ ID NO: 42;

(v) a primer set (GS-SARS22) including a primer having a nucleotide sequence as set forth in SEQ ID NO: 43 and a primer having a nucleotide sequence as set forth in SEQ ID NO: 44; and (w) a primer set (GS-SARS23) including a primer having a nucleotide sequence as set forth in SEQ ID NO: 45 and a primer having a nucleotide sequence as set forth in SEQ ID NO: 46.

The primer sets of the present invention can specifically detect SARS-CoV without reacting with other coronaviruses. That is, when PCR is performed using the primer set of the present invention, PCR products are obtained from individuals infected with SARS-CoV but no PCR products are obtained from individuals infected with other coronaviruses. The PCR primer set for SARS-CoV detection of the present invention is selected from a non-structural region and a structural region among the genome sequence of SARS-CoV. SARS-CoV regions including target nucleotide sequences for the primers according to the present invention are illustrated in FIG. 1.

The present invention also provides a method for detecting SARS-CoV, which comprises amplifying a nucleic acid sample obtained from an individual by PCR using the primer set for SARS-CoV detection.

As used herein, the term "PCR" is well known in the pertinent art. Generally, PCR includes the steps of: (a) obtaining a crude extract containing target DNA molecules from a sample; (b) adding an aqueous solution including an enzyme, a buffer, dNTPs, and oligonucleotide primers to the crude extract; (c) amplifying the target DNA molecules by two- or three-step thermal cycling (e.g., 90-96° C., 72° C., and 37-55° C.) of the resultant mixture; and (d) detecting amplified DNAs.

In the present invention, the PCR may be performed in a polypropylene tube, a 96-well plate, or a silicon-based micro PCR chip.

When the PCR is performed on a silicon-based micro PCR chip, a two-step thermal cycling as well as a three-step thermal cycling can be used. A time required for the PCR on the silicon-based micro PCR chip can be as short as 30 minutes or less. For example, the silicon-based micro PCR chip includes a silicon wafer, a surface of which is formed with a PCR chamber made by silicon lithography and the other surface is formed with a heater for heating the PCR chamber; and a glass wafer having an inlet and an outlet.

In the present invention, the PCR may be performed using 0.2-1 µM of each primer and 0.01 pg to 1 µg of a template DNA.

In the present invention, the PCR may be performed in three-step thermal cycling conditions of denaturation at 86-97° C. for 1-30 seconds, annealing at 50-70° C. for 1-30 seconds, and extension at 60-72° C. for 1-30 seconds, or in two-step thermal cycling conditions of denaturation at 86-97° C. for 1-30 seconds and annealing and extension at 50-70° C. for 5-30 seconds.

The present invention also provides a SARS-CoV detection kit including the primer set for SARS-CoV detection.

The SARS-CoV detection kit of the present invention may include the primer set, a PCR solution, a buffer, an enzyme, and the like.

Hereinafter, the present invention will be described more specifically by Examples. However, the following Examples are provided only for illustrations and thus the present invention is not limited to or by them.

EXAMPLES

Example 1

Design of Primers for SARS-CoV Detection

In this Example, there were designed PCR primers for SARS-CoV detection, which are specific to SARS-CoVs and do not react with other coronaviruses.

The genome sequences of 40 strains belonging to SARS-CoVs were searched using the public database (www.ncbi.nlm.nih.gov). Based on the search results, common sequences of the 40 strains were extracted. After sequence homology search between the common sequences and other coronaviruses and other respiratory viruses capable of infecting human bodies, homologous sequences were removed and sequences with no cross reactivity were selected. The results are presented in Table 1 below.

TABLE 1

| | Analysis results for cross reactivity using B12Seq or Blastn | | | | | | | |
|---|---|---|---|---|---|---|---|---|
| Section | H_CoV229E | H_CoV OC43 | INFV | PINFV | RSV | ADV | HMPV | Human gDNA |
| Sequence matching | NS* | NS | NS | NS | NS | NS | NS | PM** |

*NS: No significant homology
**PM: Partially matching
H_CoV229E: Human coronavirus 229E, H_CoV OC43: Human coronavirus OC43
INFV: Influenza virus type A, B, PINFV: Parainfluenza virus type 1, 2, 3
RSV: Respiratory syncytial virus type A, B
ADV: Adenovirus, HMPV: Human metapneumovirus As a result, primers as listed in Table 2 below were selected.

TABLE 2a

PCR primers for SARS-CoV detection and their characteristics

| Primer Set No. | Primer No. | Sequence | Position | Length | Tm (° C.) | PCR product (bp) |
|---|---|---|---|---|---|---|
| GS-SARS01 | A1F4 | SEQ ID NO: 1 | 3196-3221 | 26 | 58.6 | 156 |
| | A1R4 | SEQ ID NO: 2 | 3328-3351 | 24 | 58.4 | |
| GS-SARS02 | C30F4 | SEQ ID NO: 3 | 10443-10467 | 25 | 57.1 | 244 |
| | C30R4 | SEQ ID NO: 4 | 10662-10686 | 25 | 59.7 | |
| GS-SARS03 | FJF3 | SEQ ID NO: 5 | 20594-20615 | 22 | 64.1 | 266 |
| | FJR3 | SEQ ID NO: 6 | 20836-20859 | 24 | 63.8 | |
| GS-SARS04 | S2F1 | SEQ ID NO: 7 | 24097-24121 | 25 | 70.6 | 118 |
| | S2R1 | SEQ ID NO: 8 | 24187-24213 | 27 | 67.8 | |
| GS-SARS05 | CMF2 | SEQ ID NO: 9 | 26429-26454 | 26 | 60.9 | 179 |
| | CMR2 | SEQ ID NO: 10 | 26584-26607 | 24 | 59.1 | |
| GS-SARS06 | CNF2 | SEQ ID NO: 11 | 28560-28585 | 26 | 66.3 | 103 |
| | CNR2 | SEQ ID NO: 12 | 28640-28662 | 23 | 67.5 | |
| GS-SARS07 | A1F3 | SEQ ID NO: 13 | 3236-3259 | 24 | 59.2 | 184 |
| | A1R3 | SEQ ID NO: 14 | 3398-3419 | 22 | 61.3 | |
| GS-SARS08 | C30F3 | SEQ ID NO: 15 | 10443-10467 | 25 | 57.1 | 242 |
| | C30R3 | SEQ ID NO: 16 | 10659-10684 | 26 | 56.0 | |
| GS-SARS09 | FJF2 | SEQ ID NO: 17 | 20590-20615 | 26 | 68.6 | 275 |
| | FJR2 | SEQ ID NO: 18 | 20839-20864 | 26 | 69.5 | |
| GS-SARS10 | S2F3 | SEQ ID NO: 19 | 24194-24216 | 23 | 61.7 | 218 |
| | S2R3 | SEQ ID NO: 20 | 24388-24411 | 24 | 60.5 | |
| GS-SARS11 | S2F4 | SEQ ID NO: 21 | 24044-24068 | 25 | 61.8 | 167 |
| | S2R4 | SEQ ID NO: 22 | 24187-24210 | 24 | 61.4 | |
| GS-SARS12 | CMF1 | SEQ ID NO: 23 | 26429-26454 | 26 | 60.9 | 275 |
| | CMR1 | SEQ ID NO: 24 | 26677-26703 | 27 | 64.4 | |
| GS-SARS13 | CNF4 | SEQ ID NO: 25 | 28643-28666 | 24 | 68.4 | 145 |
| | CNR4 | SEQ ID NO: 26 | 28764-28787 | 24 | 67.3 | |
| GS-SARS14 | CNF5 | SEQ ID NO: 27 | 28645-28666 | 22 | 64.9 | 140 |
| | CNR5 | SEQ ID NO: 28 | 28764-28784 | 21 | 66.5 | |
| GS-SARS15 | A1F1 | SEQ ID NO: 29 | 3156-3179 | 24 | 65.1 | 267 |
| | A1R1 | SEQ ID NO: 30 | 3398-3422 | 25 | 65.4 | |
| GS-SARS16 | A1F2 | SEQ ID NO: 31 | 3231-3256 | 26 | 60.7 | 121 |
| | A1R2 | SEQ ID NO: 32 | 3327-3351 | 25 | 60.9 | |
| GS-SARS17 | C30F1 | SEQ ID NO: 33 | 10441-10467 | 27 | 59.2 | 246 |
| | C30R1 | SEQ ID NO: 34 | 10660-10686 | 27 | 61.2 | |
| GS-SARS18 | C30F2 | SEQ ID NO: 35 | 10190-10214 | 25 | 64.7 | 102 |
| | C30R2 | SEQ ID NO: 36 | 10265-10291 | 27 | 55.2 | |
| GS-SARS19 | FJF1 | SEQ ID NO: 37 | 20701-20728 | 28 | 60.5 | 115 |
| | FJR1 | SEQ ID NO: 38 | 20794-20815 | 22 | 56.2 | |
| GS-SARS20 | S2F2 | SEQ ID NO: 39 | 24042-24068 | 27 | 64.2 | 175 |
| | S2R2 | SEQ ID NO: 40 | 24191-24216 | 26 | 64.8 | |
| GS-SARS21 | S2F5 | SEQ ID NO: 41 | 24492-24516 | 25 | 61.8 | 123 |
| | S2R5 | SEQ ID NO: 42 | 24595-24614 | 20 | 65.5 | |
| GS-SARS22 | CNF1 | SEQ ID NO: 43 | 28641-28666 | 26 | 70.2 | 151 |
| | CNR1 | SEQ ID NO: 44 | 28766-28791 | 26 | 70.0 | |
| GS-SARS23 | CNF3 | SEQ ID NO: 45 | 28640-28666 | 27 | 72.1 | 150 |
| | CNR3 | SEQ ID NO: 46 | 28764-28789 | 26 | 71.9 | |

Example 2

Tube RT-PCR for SARS-CoV RNA Samples

In this Example, RT-PCR was performed on a PCR machine (ABI 2400) using the primer sets of GS-SARS01-06 and SARS-CoV RNA (total RNA samples extracted from SARS-CoVs) as templates. At this time, the concentration of the templates was 2 μg/20 μl. Before initiating PCR, the RNA samples in a 25 μl PCR solution were converted to cDNAs by reverse transcription at 42° C. for 60 minutes. The PCR was performed in three-step thermal cycling conditions as follows: 50 cycles of denaturation at 95° C. for 20 seconds, annealing 65° C. for 40 seconds, and extension at 72° C. for 60 seconds.

The results are shown in FIG. 2. As shown in FIG. 2, SARS-CoV RNAs were detected. In FIG. 2, lane 1 is 1 kb-DNA plus ladder (Invitrogen), lane 2 is a PCR product (156 bp) amplified with GS-SARS01, lane 3 is a PCR product (244 bp) amplified with GS-SARS02, lane 4 is a PCR product (179 bp) amplified with GS-SARS05, lane 5 is a PCR product (103 bp) amplified with GS-SARS06, and lane 6 is a PCR product (118 bp) amplified with GS-SARS04.

Example 3

RT-PCR for SARS-CoV RNA Samples on Silicon-Based PCR Chip

In this Example, RT-PCR was performed on a PCR machine (GenSpector 1&2) using the primer sets of GS-SARS01-06 and SARS-CoV RNAs (total RNA samples extracted from SARS-CoVs) as templates. At this time, the concentration of the templates was $2.4\times10^3$ copies. Before initiating PCR, the RNA samples in a 1 μl at PCR solution on a silicon-based PCR chip were converted to cDNAs by reverse transcription at 42° C. for 60 minutes. The PCR was performed in three-step thermal cycling conditions as follows: 50 cycles of denaturation at 92° C. for 1 second, annealing 52° C. for 1 second, and extension at 72° C. for 5 seconds.

Figure 2:
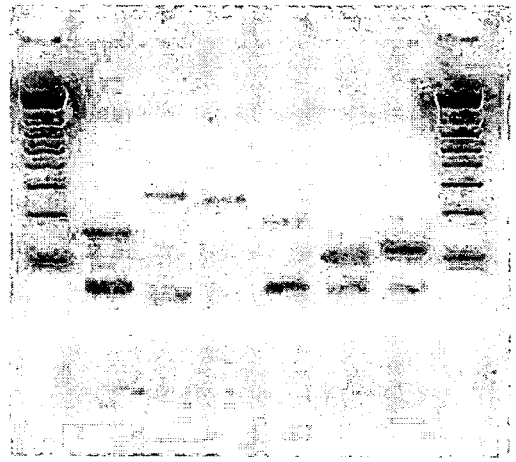
FIG. 2 illustrates tube RT-PCR results for SARS-CoV RNA samples using primers according to the present invention.
Figure 3:
FIG. 3 illustrates PCR results for SARS-CoV RNA samples on a silicon-based PCR chip using primers according to the present invention.

The results are shown in FIG. 3. As shown in FIG. 3, SARS-CoV RNAs were detected on the silicon-based PCR chip. Each lane of FIG. 3 is as defined in FIG. 2.

Example 4

Cross Reactivity Test with Human gDNAs

In this Example, whether the primer sets of GS-SARS01-14 react with human gDNAs was analyzed.

PCR was performed in the same manner as in Example 3 except that 45 cycles were repeated using a 25 µl PCR solution containing 1 ng SARS-CoV cDNAs+200 ng human gDNAs as templates.

Figure 4:
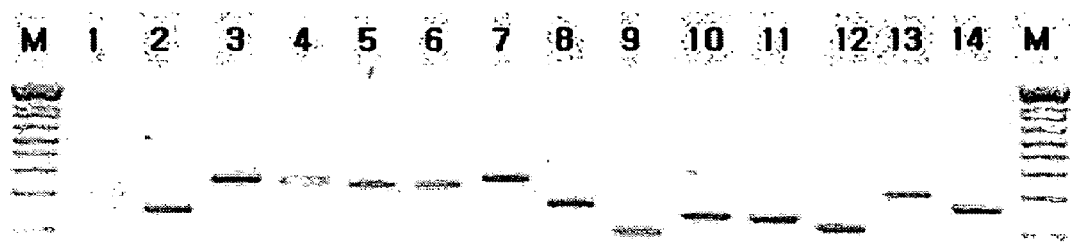
FIG. 4 illustrates PCR results for SARS-CoV RNA samples and human gDNA samples on a silicon-based PCR chip using primers according to the present invention.

The results are shown in FIG. 4. As shown in FIG. 4, no cross reactivity with human gDNAs were observed and SARS-CoV RNAs were detected. In FIG. 4, M is 1 kb-DNA plus ladder (Invitrogen), lane 1 is a PCR product (184 bp) amplified with GS-SARS07, lane 2 is a PCR product (156 bp) amplified with GS-SARS01, lane 3 is a PCR product (275 bp) amplified with GS-SARS09, lane 4 is a PCR product (266 bp) amplified with GS-SARS03, lane 5 is a PCR product (242 bp) amplified with GS-SARS08, lane 6 is a PCR product (244 bp) amplified with GS-SARS02, lane 7 is a PCR product (275 bp) amplified with GS-SARS12, lane 8 is a PCR product (179 bp) amplified with GS-SARS05, lane 9 is a PCR product (103 bp) amplified with GS-SARS03, lane 10 is a PCR product (145 bp) amplified with GS-SARS13, lane 11 is a PCR product (140 bp) amplified with GS-SARS14, lane 12 is a PCR product (118 bp) amplified with GS-SARS04, lane 13 is a PCR product (218 bp) amplified with GS-SARS10, and lane 14 is a PCR product (167 bp) amplified with GS-SARS11.

As apparent from the above description, a primer set of the present invention can be efficiently used in a method for specifically detecting SARS-CoV.

A method for detecting SARS-CoV of the present invention can detect SARS-CoV without cross reaction of the primer set with other coronaviruses.

A SARS-CoV detection kit of the present invention can be used in specifically detecting SARS-CoV.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A primer set (GS-SARS01) comprising a primer consisting of SEQ ID NO: 1 and a primer consisting of SEQ ID NO: 2, wherein the primer set specifically amplifies a target region of Severe Acute Respiratory syndrome corona virus (SARS-CoV) in a polymerase chain reaction (PCR) and the primers do not share sequence homology with human coronavirus 229E, human coronavirus OC43, influenza virus type A, influenza virus type B; parainfluenza virus types 1, 2, or 3; respiratory syncytial virus type A, respiratory syncytial virus type B; or human metapneumovirus.

2. A method for detecting SARS-CoV, which comprises amplifying a nucleic acid sample obtained from an individual by PCR using the primer set of claim 1.

3. The method of claim 2, wherein the PCR is performed in a polypropylene tube, a 96-well plate, or a silicon-based micro PCR chip.

4. The method of claim 2, wherein the PCR is a two-step PCR comprising a denaturation step and an annealing and extension step or a three-step PCR comprising a denaturation step, an annealing step, and an extension step.

5. The method of claim 2, wherein the PCR is performed using 0.2-1 μM of each primer and 0.01 pg to 1 μg of a template DNA.

6. The method of claim 2, wherein a time required for the PCR on a silicon-based micro PCR chip is 30 minutes or less.

7. The method of claim 2, wherein the PCR is performed in three-step thermal cycling conditions of denaturation at 86-97° C. for 1-30 seconds, annealing at 50-70° C. for 1-30 seconds, and extension at 60-72° C. for 1-30 seconds, or in two-step thermal cycling conditions of denaturation at 86-97° C. for 1-30 seconds and annealing and extension at 50-70° C. for 5-30 seconds.

8. The method of claim 6, wherein the silicon-based micro PCR chip comprises:

a silicon substrate, a surface of which is formed with a PCR chamber made by silicon lithography and the other surface is formed with a heater for heating the PCR chamber; and a glass substrate having an inlet and an outlet.

9. A SARS-CoV detection kit comprising the primer set of claim 1.

* * * * *